United States Patent [19]

Dowling, Jr. et al.

[11] Patent Number: 4,785,171
[45] Date of Patent: Nov. 15, 1988

[54] FINGERPRINT ACQUISITION SYSTEM WITH A FIBER OPTIC BLOCK

[75] Inventors: Robert F. Dowling, Jr., Woodstock; Keith L. Knowlton, Brooklyn, both of Conn.

[73] Assignee: Fingerprint Technology, Inc., Pomfret, Conn.

[21] Appl. No.: 3,615

[22] Filed: Jan. 15, 1987

[51] Int. Cl.⁴ .............................................. H01J 5/16
[52] U.S. Cl. ..................................... 250/227; 356/71; 382/4
[58] Field of Search ......................... 250/227; 356/71; 350/96.25, 96.26, 96.27; 382/4

[56] References Cited

U.S. PATENT DOCUMENTS

| | | | |
|---|---|---|---|
| 3,247,756 | 4/1966 | Siegmund | 88/1 |
| 3,323,407 | 6/1967 | Gamba | 88/1 |
| 3,435,244 | 2/1969 | Burckhardt et al. | 250/219 |
| 3,453,596 | 7/1969 | Hawkins | 356/71 |
| 3,630,612 | 12/1971 | Lehovec | 350/96.25 |
| 3,648,240 | 5/1972 | Jacoby et al. | 340/146.3 E |
| 3,668,633 | 6/1972 | Sadowsky | 340/146.3 E |
| 4,032,889 | 6/1977 | Nassimbene | 250/227 |
| 4,120,585 | 10/1978 | DePalma et al. | 356/71 |
| 4,210,899 | 7/1980 | Swonger et al. | 340/146.3 E |
| 4,322,163 | 3/1982 | Schiller | 356/71 |
| 4,537,484 | 8/1985 | Fowler et al. | 382/4 |
| 4,544,267 | 10/1985 | Schiller | 356/71 |
| 4,544,842 | 10/1985 | Engemann et al. | 250/227 |
| 4,547,668 | 10/1985 | Tsikos | 250/227 |
| 4,553,837 | 11/1985 | Marcus | 356/71 |
| 4,569,080 | 2/1986 | Schiller | 382/4 |
| 4,582,985 | 4/1986 | Lofberg | 235/380 |
| 4,671,612 | 6/1987 | Sakurai et al. | 350/96.27 |

Primary Examiner—David C. Nelms
Attorney, Agent, or Firm—Hayes & Reinsmith

[57] ABSTRACT

A characteristic pattern acquisition system provides a block comprised of a bundle of optical fibers longitudinally aligned in parallel relation each having an imaging end perpendicular to a major longitudinal axis of the block and a detecting end which is angled, and a source of light directed toward through the imaging end to illuminate the detecting end, the detecting end serving to reflect internal light rays only when the medium outside the detecting end of each fiber has a refractive index less than the optical medium of the fibers. The composite reflection of light from the angled surfaces of the fibers create at the imaging end a reproduction of a characteristic pattern such as the relief features of a fingertip applied to the detecting end of the fiberoptic block. Means are directed toward the imaging end of the fiberoptic block for electronically transmitting an image thereon of the characteristic pattern which is placed on the fiberoptic block detecting end.

26 Claims, 4 Drawing Sheets

FINGERPRINT ACQUISITION SYSTEM WITH A FIBER OPTIC BLOCK

BACKGROUND OF THE INVENTION

This invention relates to a system for acquiring fingerprints and other characteristic patterns and, more specifically, to a system utilizing a fiberoptic block to detect and transmit a characteristic pattern image for analysis.

Several fingerprint acquisition systems have been reported in the art.

U.S. Pat. No. 3,668,633 to Sadowsky discloses the use of separate arrays of optical fibers for transmitting light to a finger and for receiving a fingerprint reflection.

U.S. Pat. No. 4,582,985 to Lofberg discloses the use of an array of sensing elements to detect a fingerprint. Each sensing element is attached to a single optical fiber which carries light from an LED to a finger and which also carries the light reflected from the fingerprint back to a phototransistor which then processes the fingerprint image electronically. The finger is disclosed as being spaced from the fiber end which is shown as having an end face slightly curved but generally perpendicular to its axis.

A number of other patents disclose the use of transparent blocks upon which a finger is placed and through which a detecting light signal is internally reflected at less than the critical angle with respect to the block surface. The internally reflected light signal carries the image of the fingerprint as a result of selective light absorption at the fingerprint ridges. These patents are U.S. Pat. Nos. 4,120,535 to De Palma et al, 4,553,837 to Marcus, 4,210,899 to Swonger et al, 4,537,484 to Fowler et al, 4,032,889 to Nassimbene, and 4,553,267 and 4,322,163, both to Schiller.

These prior art fingerprint acquisition systems in general utilize complex, costly and fragile components, especially those adapted for detecting the fingerprint itself. In addition, these systems do not always offer the high resolution and detail required for high accuracy fingerprint definition. Because of such problems, these conventional systems are typically not suited for widespread use and are generally confined to a narrow range of applications which justify complexity and expense.

Bearing in mind these and other deficiencies of the prior art, it is an object of the present invention to provide a means for acquiring fingerprints and other characteristic patterns which offers considerable simplicity in design and construction.

It is another object of the present invention to provide a fingerprint acquisition system which has high resolution capability.

It is a further object of the present invention to provide a fingerprint acquisition system which is intended for widespread security and identification applications.

It is another object of the present invention to provide a means for acquiring fingerprints and other characteristic patterns which has high durability in repeated use.

Other objects will be in part obvious and in part pointed out in more detail hereinafter.

A better understanding of the objects, advantages, features, properties and relations of the invention will be obtained from the following detailed description and accompanying drawings which set forth an illustrative embodiment and is indicative of the way in which the principle of the invention is employed.

SUMMARY OF THE INVENTION

The present invention provides a characteristic pattern acquisition system comprising a fiberoptic block having a first end face for detecting a characteristic pattern placed thereon and a second imaging end face, opposite the first detecting end face, for projecting an image of a characteristic pattern placed upon the detecting end face, the fiberoptic block comprising a bundle of optical fibers having light ray-guiding cores, the optical fibers having opposite free end faces terminating in and forming the detecting and imaging end faces, respectively, the individual optical fiber detecting end faces each being angled such that when there is present outside the fiber end face a medium having an index of refraction less than that of the fiber core parallel light rays in the fiber core are prevented from exiting through the fiber end face while at least a portion of non-parallel light rays in the fiber core are permitted to internally reflect at the fiber end and reverse direction in the fiber; and means for electronically transmitting the image of a characteristic pattern placed upon the fiberoptic block detecting end face.

DETAILED DESCRIPTION OF THE INVENTION

The present invention comprises a system to electronically acquire fingerprints, palm prints, toe prints or other patterns using fiberoptic and electronic components. These various patterns are herein referred to collectively as "characteristic patterns". With the present invention it is possible to obtain and electronically transmit to a computer memory or other electronic device an individual's fingerprint or other characteristic pattern virtually instantaneously and without the use of any type of ink. Using known pattern recognition technology, this stored characteristic pattern may then be recalled at any time and electronically compared to another characteristic pattern being detected by the fiberoptic block to ascertain if the two patterns are the same. While this system is contemplated to be most useful for security purposes by controlling access to certain areas or equipment, other applications will become obvious as the reader gains a complete understanding of the way in which the system functions. The present invention may also be useful to detect other characteristic patterns beyond those on the skin.

Figure 1:
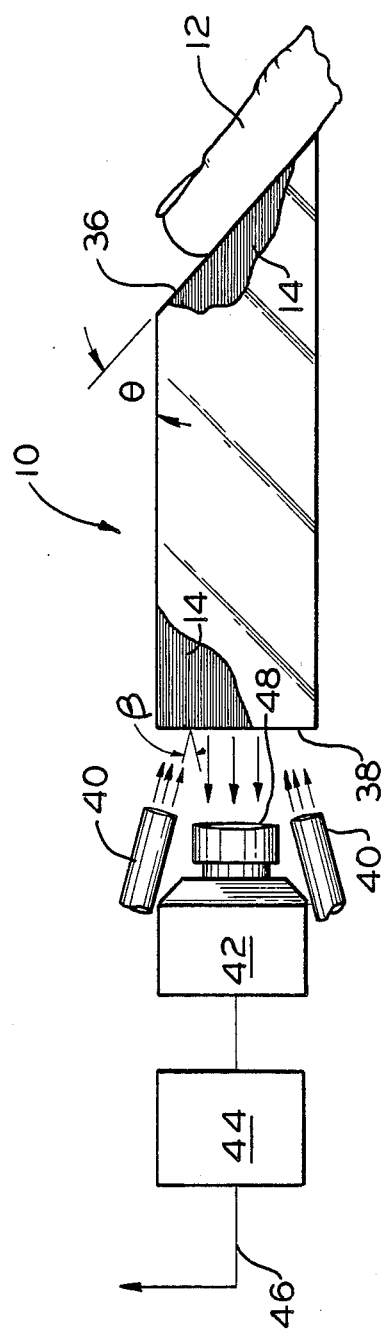
FIG. 1 is a side view of a fiberoptic block of the present invention in relation to a light source, a camera, and a schematic representation of a skin pattern comparing and matching means of the present invention.
Figure 2:
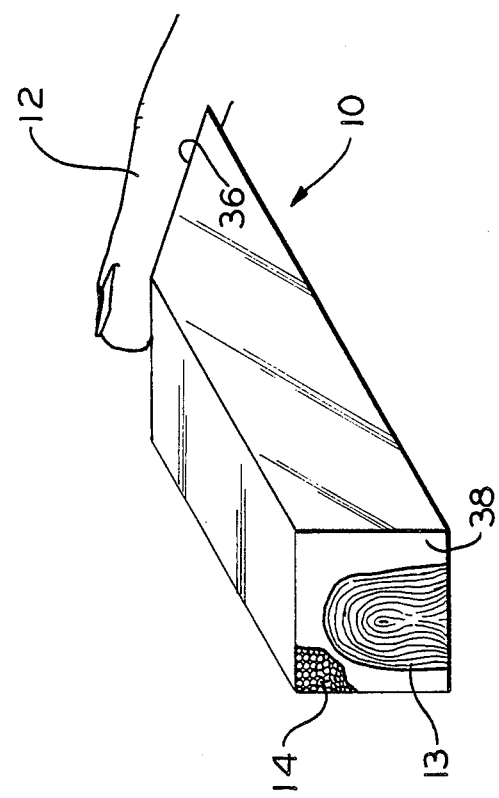
FIG. 2 is a perspective view of the fiberoptic block of FIG. 1.

In FIGS. 1 and 2 there is shown a characteristic pattern acquisition system comprising a fiberoptic block 10 for detecting a characteristic skin pattern, for example, from a tip of a finger 12 as shown. The partial detail sections of the fiberoptic block 10 in FIGS. 1 and 2 show that the individual optic fibers 14 are arrayed in a bundle to make up the fiberoptic block with each optical fiber being in essentially parallel directly adjacent relationship to the other. Each optical fiber 14 is of conventional structure and consists of a light guiding core surrounded by a cladding material. The cladding material has an index of refraction lower than that of the core material, thereby enabling suitably directed light rays within the core to be reflected at the core/cladding interface and propagate through the length of the core. Any known type of optical fiber may be utilized in the fiberoptic block of the present invention. Examples of suitable optical fibers are those having cores of glass, fused silica or a polymer such as an acrylate or methacrylate. Any of the conventional glass or polymer cladding materials may be utilized. Preferably the optical fiber core and cladding are composed of Schott type F2 (flintglass) and Schott type 8250 (borosilicate), respectively, with indicies of refraction of 1.62 and 1.48, respectively. These types of glass are available from Schott Optical Co., Duryea, PA. The individual optical fibers may be fused together in the bundle, or held by a conventional adhesive, or may be confined by mechanical means. The fused technique is preferable, for example, by the process disclosed in U.S. Pat. No. 3,247,756 to Siegmund.

The individual optical fibers 14 have polished core-exposing end faces 16 (FIG. 3) at angle theta with respect to a major longitudinally extending fiber axis. The individual angled fiber end faces 16 form the fiberoptic block end face 36 which is also at angle theta with respect to the major axis of the individual optical fibers 14. A finger 12 or other portion of skin having a characteristic pattern of ridges is placed against the angled fiberoptic end face 36 for detection of that characteristic pattern. As will be explained more fully below, when a light source 40 directs light rays into the individual optical fibers 14 toward the angled end face 36, an image 13 (FIG. 2) of the characteristic skin pattern will be detected and displayed on the fiberoptic block imaging end 38 opposite angled end face 36. This image producing end face 38 is formed by the polished free ends of optical fibers 14 opposite the angled end faces 16. The image 13 from end face 38 is then received by a photosensitive device, here shown as camera 42 (FIG. 1), for storage and/or further processing.

Figure 3:
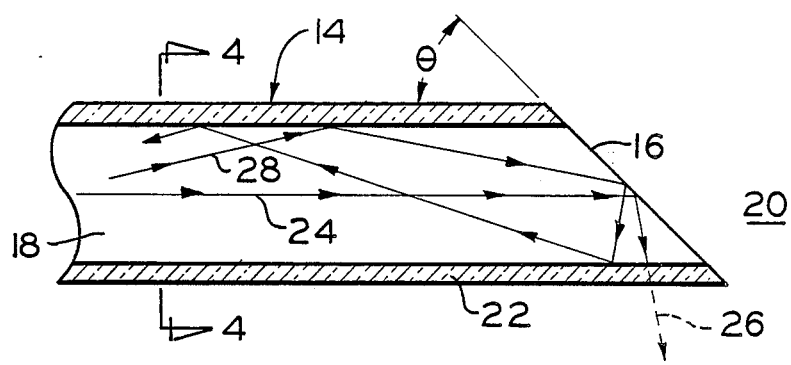
FIG. 3 is an enlarged longitudinal cross-sectional view, partly broken away, of the angled end of an individual optical fiber of the fiberoptic block of FIG. 1.

As shown in detail in FIG. 3, each individual optical fiber 14 has an end face 16 having angle theta with respect to the major fiber axis. Angle theta is selected so as to prevent the escape of parallel fiber light rays through the angled end face 16 of the fiber core 18 when there is present outside the end face 16 a medium 20 having an index of refraction less then that of the fiber core 18. The term "parallel" is here used with relation of the major axis of the individual optical fiber. Parallel light rays are also termed axial or meridian light rays. The angle theta is a function of the index of refraction of the optical fiber core 18 and the index of refraction of the fiber cladding 22 and the surrounding medium 20, in this case, air. The angle theta is defined by the relationship (from Snell's Law):

$$0 \leq \cos^{-1}(n_2/n_1)$$

wherein
$n_2$ = index of refraction of surrounding media
$n_1$ = index of refraction of fiber core This relationship is, naturally, only theoretical and may be affected by various factors such as material purity and surface effects.

Where the surrounding media is air and where the aforedescribed preferred core and cladding materials are utilized, the angle theta is preferably in the range of about 30° to 60° and, more preferably, about 45°.

As shown in FIG. 3, parallel light rays within the optical fiber strike the angled end face 16 and are internally reflected toward cladding 22. The angles shown in the drawings are not meant to be to scale but merely for reference purposes. Many, if not most, of light rays 24 internally reflecting off the optical fiber angled end face 16 will be transmitted out of the fiber through the cladding, as shown by dotted light ray line 26. Since the light ray 26 could enter an adjacent fiber, thus reducing the contrast of the characteristic pattern at the imaging end face, it may be advantageous to utilize an optically absorbant material around each fiber 14 in block 10. A black glass of this type is disclosed in the aforementioned Siegmund patent.

Figure 4:
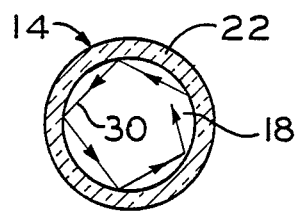
FIG. 4 is a radial cross-sectional view of the optical fiber of FIG. 3 taken along line 4—4.

Despite the transmission of many light rays 26 out of the fiber, a portion of the non-parallel fiber light rays 28 traveling toward the optical fiber angled end face will be reflected back from that end in the opposite fiber direction toward the imaging end face. This reflective light is believed to occur principally from non-parallel rays of light which travel through the optical fiber in a spiral fashion. In FIG. 4 there is depicted a typical spiral ray 30 as it propagates in a counter clockwise manner through the fiber, as shown in a radial cross section of fiber 14. Because these spiral rays always reflect off the end face 16 at a compound angle, they may be propagated through the optical fiber at angles much different than would be indicated in a two dimensional representation as in FIG. 3. For this reason some of these spiral rays are ultimately reflected back from the angled fiber end face 16 and through the optical fiber in the opposite direction.

Figure 5:
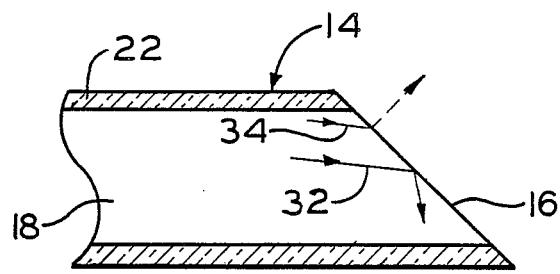
FIG. 5 is another enlarged longitudinal cross-sectional view of the angled end of an individual optical fiber of the fiberoptic block of FIG. 1.

To demonstrate the manner in which a contrasting image is produced by the present invention, in FIG. 5 there are shown two light rays 32, 34 striking an angled optical fiber end face 16 in the fiberoptic block of the present invention. If a light transmitting medium having an index of refraction less than that of the fiber core is present on the outside of the optical fiber end face 16, for example, air having an index of refraction of 1.00, fiber light ray 32 striking the end face will tend to be reflected internally, and at least a portion of non-parallel light rays will be reflected back through the fiber away from the angled end face. However, should there be present on the outside of the optical fiber end face 16 a light absorbing medium or a medium having a index of refraction equal to or greater than that of the fiber core 18, for example, a ridge of a fingerprint, then light ray 34 striking the angled end face 16 will tend not to be reflected internally at the end face and will be instead absorbed. This is shown by the dotted absorbed light ray in FIG. 5. Consequently, where there is no air space between end face 16 and such light absorbing medium, few or no light rays will be reflected back through the fiber 14 away from the angled end face 16.

Referring back to FIGS. 1 and 2, the fiberoptic block 10 is composed of a large number of individual optical fibers 14. The diameter of each fiber is smaller than the width of a ridge on a fingerprint or other characteristic skin pattern. Typically, the fibers are between about 3 and about 50 microns in diameter. Each optical fiber then will tend to reflect at least some light, e.g., spiral light rays, when a skin ridge is not contacting its end face, and will tend not to reflect back any light when a skin ridge is contacting its end face. Thus, when the end 38 of the fiberoptic block is illuminated, as shown in FIG. 1, the individual reflection or non-reflection of the fibers 14 at angled block end 36 will produce a fingerprint image on end 38 of fiberoptic block 10 opposite its angled end face 36, as shown in FIG. 2.

A reduction in the diameter of the fibers would increase the resolution of the image and thus create the capacity for greater detail. However, this increased number of fibers also increases the cost of the block. The optimum number and size of the fibers 14 can be determined by simple experimentation. Typically the size of the fiberoptic block would be approximately 1.25 inches square and 1 to 2 inches in length. This size works well for individual fingerprints. Larger blocks could be produced for palm prints, baby footprints, or other characteristic pattern applications.

Because the actual finger is placed on the fiberoptic block angled end face 36 and the fingerprint image is projected onto the shorter opposite fiberoptic block end face 38, the fingerprint image 13 length is reduced by the ratio of the lengths of the two fiberoptic block ends. The width of the print remains unchanged. This length reduction would be of minimal concern in a system where all of the fingerprint images stored for comparison came from fiberoptics blocks having the same angle face. However, if this system were to be used to compare a shortened fingerprint image from a fiberoptic block with an actual size image, this shortening may not be acceptable. Means should then be provided, for example, by programming a conventional digital computer 44 (FIG. 1), to restore the shortened image 13 to actual size and dimension so that correct comparisions may be made between a fingerprint image from the fiberoptic block and a fingerprint image on file. Such programs are well known in the industry, one such program being sold under the name "Image Pro", developed and marketed by Media Cybernetics Co., Silver Spring, MD.

A typical application of the invention is shown in FIG. 1 comprising light sources 40 for illuminating the imaging end 38 of fiberoptic block 10 and a video camera 42 for receiving the image 13 from the fingertip 12. The fingerprint image 13 is processed by the camera 42 and sent to a computer 44, for example, for comparing the received characteristic pattern image with another characteristic pattern image and determining a match between the two. The ouput signal 46 from the computer 44 as a result of a match or mismatch between the detected and stored fingerprint could be used to activate an access device (not shown), for example, a door in a security area.

The illuminating light source 40 is positioned to provide even illumination to all ends of the optical fibers 14 at fiberoptic block end 38 and to insure that light rays will enter the fibers 14 and propagate down the length of the cores of the optical fibers 14 towards the detecting end 36 of fiberoptic block 10. The actual source of light may be conventional light bulbs, fluorescent tubes or light emitting diodes, which may emit visible or other light.

A photosensitve device, shown in FIG. 1 as video camera 42, is used to electronically transmit the fingerprint image 13 on the imaging end 38 of the fiberoptic block to the computer 44 for matching the fingerprint image 13 with another fingerprint image. Preferably a solid state camera of a charge-coupled device (CCD) type is employed because of its freedom from distortion and the concise imaging data which it produces. A typical camera of this type is sold by Pulnix America Co., Sunnyvale, CA as model TM-540-R. The computer then converts the standard video signal output from camera 42 to digital data from analysis. The silicon-based image detectors employed in CCD cameras are highly sensitive to infrared energy at approximately 800 nanometers wave length. This permits the use of low cost infrared light-emitting diodes as light source.

If desired to activate multiple devices or displays in a given application, multiple fiberoptic block and camera assemblies may be connected to computer 14.

It has been found that placement of light source 40 in close proximity to the lens 48 of camera 42 results in the best quality of image 13 on block imaging end 38. However, it is important that when the light source and camera are spaced apart from the iamging end 38 as shown in FIG. 1, light source 40 and camera lens 48 be positioned relative to the polished surface of imaging end 38 so as to avoid "specular" or "first surface" reflection wherein light rays from light source 40 are reflected off the polished imaging end 38 surface directly into lens 48. This specular reflection will cause camera 42 to pick up a reflected image of the light source itself rather than an image of the characteristic pattern placed on the block detecting end 36. The proper relative positioning of the light source 40, camera lens 48 and block imaging end 38 can be determined by simple experimentation.

Figure 7:
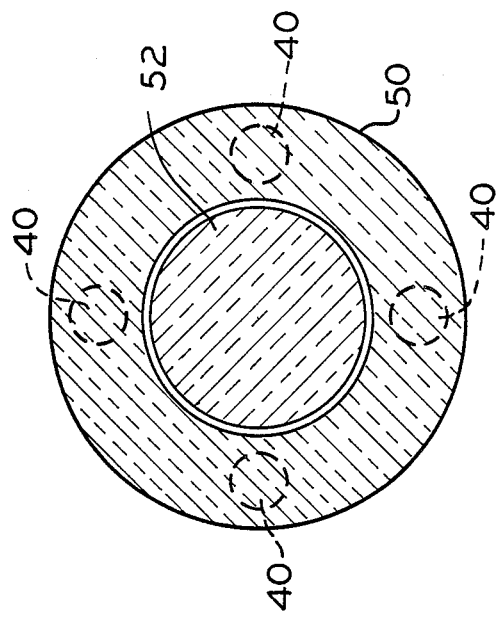
FIG. 7 is a front view of the polarizing lenses of FIG. 6.
Figure 6:
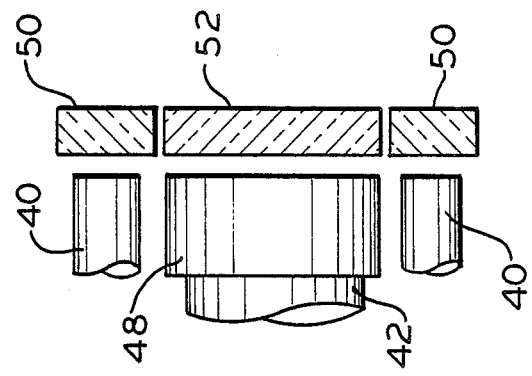
FIG. 6 is a sectional side view of a light source, electronic image-transmitting camera, and polarizing lenses useful in one embodiment of the present invention.

To prevent specular reflection, it is also possible to employ separate cross-polarizing filters over the light source and camera lens, respectively. As seen in FIGS. 6 and 7, in side and front views, respectively, light sources 40 are disposed in a ring pattern around camera lens 48 for even illumination of a fiberoptic block imaging end. An annular disk shaped transparent polarizing filter 50 is disposed over light sources 40 for polarizing the light rays therefrom before they strike the block imaging end. A circular disk shaped transparent polarizing filter 52 is disposed over camera lens 48 for polarizing the light received from the block imaging end. Polarizing filters 50 and 52 may be rotated relative to one another to a 90° relative position to cross polarize and block specular reflection from the surface of the imaging end without blocking the light rays carrying the characteristic pattern image. With the use of the aforementioned cross-polarizing filters, light sources 40 and camera lens 48 may be positioned at any angle relative to the imaging end 38 of the fiberoptic block without regard for any specular reflection problem.

Thus, as described above, the present invention provides a means for acquiring characteristic patterns which is simple in design and construction while being durable under repeated use. The high resolution available with the use of the disclosed fiberoptic block makes the present invention highly useful for widespread security applications where fingerprints or other characteristic patterns are used for identification. The electronic output of the desired characteristic pattern images may be transmitted by wire, radio or other transmission means to conventional computer systems for comparison and matching with other stored patterns.

As will be apparent to persons skilled in the art, various modifications, adaptations and variations of the foregoing specific disclosure can be made without departing from the spirit and scope of this invention.

Having thus described the invention, what is claimed is:

1. A characteristic pattern acquisition system comprising:
   a fiberoptic block having a first end face for detecting a characteristic pattern placed thereon and a second imaging end face, the imaging end face being opposite the detecting end face for projecting an image of a characteristic pattern placed upon said detecting end face and for receiving light rays from a light source, said fiberoptic block comprising a bundle of optical fibers in adjacent parallel relationship having light ray-guiding cores, the optical fibers having opposite free end faces terminating in and forming said detecting and imaging end faces, respectively, the individual optical fiber detecting end faces each being angled such that when there is present outside the fiber detecting end face a medium, having an index of refraction less than that of the fiber core, parallel light rays in said fiber core are prevented from exiting through the fiber detecting end face while at least a portion of non-parallel light rays in said fiber core are permitted to internally reflect at the fiber detecting end face and reverse direction in said fiber;
   a light source directed through the imaging end face of the fiberoptic block to illuminate a characteristic pattern placed upon the detecting end face of the fiberoptic block, and
   means directed toward the imaging end face of the fiberoptic block for electronically transmitting said image of a characteristic pattern placed upon said fiberoptic block detecting end face.

2. The system of claim 1 wherein said optical fibers in said fiberoptic block have a diameter of from about 3 to 50 microns.

3. The system of claim 2 wherein said fiberoptic block detecting end face and said individual optical fiber detecting end faces have an angle from about 30° to about 60°, relative to the longitudinal axis of said optical fibers.

4. The system of claim 1 further including means for comparing the electronically transmitted characteristic pattern with another characteristic pattern and determining a match therebetween.

5. The system of claim 1 including electronic means to correct shortening of a characteristic pattern detected by said fiberoptic block.

6. The system of claim 1 wherein said electronic transmitting means comprises a video camera.

7. The system of claim 1 further including a light source directed through said imaging end face of said fiberoptic block to illuminate a characteristic pattern placed upon said detecting end face.

8. The system of claim 7 wherein said electronic transmitting means comprises a video camera.

9. The system of claim 8 wherein said camera and said light source are spaced apart from said fiberoptic block imaging end face and positioned to prevent specular reflection of light from said light source off said imaging end face and into said camera.

10. The system of claim 8 wherein said camera and said light source are spaced apart from said fiberoptic block imaging end face, and wherein said system further includes separate polarizing filters over said camera and said light source, said polarizing filters being set at relative cross-polarizing positions to block specular reflection of light from said light source off said imaging end face and into said camera.

11. The system of claim 8 wherein said camera is of the charge-coupled device type and wherein said light source is an infrared light-emitting diode.

12. The system of claim 8 wherein said camera includes a lens and and wherein said light source is positioned in a ring pattern around said camera lens.

13. The system of claim 4 wherein said image comparing means comprises a digital computer for storing, retrieving and comparing characteristic patterns.

14. The system of claim 4 further including means for activating an access device operable by said comparing and match determining means.

15. The system of claim 1 wherein said fiberoptic block end face is sized to receive a human fingertip.

16. The system of claim 1 wherein said fiberoptic block detecting end face is sized to receive a human palm.

17. A characteristic pattern acquisition system comprising:
   a fiberoptic block having a first end face for detecting a characteristic pattern placed thereon and a second imaging end face, opposite the first detecting end face, for projecting an image of a characteristic pattern placed upon said detecting end face, said fiberoptic block comprising a bundle of adjacent essentially parallel optical fibers having light ray-guiding cores, the optical fibers having opposite free end faces terminating in and forming said detecting and imaging end faces, respectively, the individual optical fiber detecting end faces each being angled such that, when there is present outside the fiber detecting end face a medium having an index of refraction less than that of the fiber core, parallel light rays in said fiber core are prevented from exiting through the fiber detecting end face while at least a portion of non-parallel light rays in said fiber core are permitted to internally reflect at the fiber detecting end face and reverse direction in said fiber;
   a light source directed through said imaging end face of said fiberoptic block to illuminate a characteristic pattern placed upon said detecting end face; and
   a video camera directed toward the imaging end face of the fiberoptic block for electronically transmitting said image of a characteristic pattern placed upon said fiberoptic block detecting end face.

18. The system of claim 17 wherein said optical fibers in said fiberoptic block have a diameter of from about 3 to 50 microns.

19. The system of claim 18 wherein said fiberoptic block detecting end face and said individual optical fiber angled end faces have an angle from about 30° to about 60°, relative to the axis of said optical fibers.

20. The system of claim 19 further including a digital computer for comparing the electronically transmitted characteristic pattern with another characteristic pattern determining a match therebetween, electronic means to correct shortening of a characteristic pattern detected by said fiberoptic block; and means for activating an access device operable by said digital computer.

21. The system of claim 19 wherein said camera and said light source are spaced apart said fiberoptic block imaging end face and positioned to prevent specular reflection of light from said light source off said imaging end face and into said camera.

22. The system of claim 19 wherein said camera and said light source are spaced apart from said fiberoptic block imaging end face, and wherein said system further includes separate polarizing filters over said camera and said light source, said polarizing filters being set at relative cross-polarizing positions to block specular reflection of light from said light source off said imaging end face and into said camera.

23. The system of claim 19 wherein said camera is of the solid state charge-coupled device type and wherein said light source is an infrared light-emitting diode.

24. The system of claim 19 wherein said camera includes a lens and and wherein said light source is positioned in a ring pattern around said camera lens.

25. The system of claim 19 wherein said fiberoptic block end face is sized to receive a human fingertip.

26. The system of claim 19 wherein said fiberoptic block detecting end face is sized to receive a human palm.

* * * * *

UNITED STATES PATENT AND TRADEMARK OFFICE
CERTIFICATE OF CORRECTION

PATENT NO. : 4,785,171

DATED : November 15, 1988

INVENTOR(S) : Keith L. Knowlton and Robert Dowling

It is certified that error appears in the above-identified patent and that said Letters Patent is hereby corrected as shown below:

Column 1, line 34, wherein the number "4,120,535" should read --4,120,585--.

Signed and Sealed this

Fifteenth Day of August, 1989

Attest:

DONALD J. QUIGG

Attesting Officer

Commissioner of Patents and Trademarks